United States Patent
Rogers et al.

(10) Patent No.: US 11,079,377 B2
(45) Date of Patent: Aug. 3, 2021

(54) NANOPORE COATING FOR SENSING CHEMICAL BOND FORMATION

(71) Applicant: International Business Machines Corporation, Armonk, NY (US)

(72) Inventors: Priscilla Racquel Rogers, Fitzroy (AU); Stefan Harrer, Hampton (AU); Ali Afzali-Ardakani, Ossining, NY (US); Jose Miguel Lobez Comeras, New York, NY (US); Sung Cheol Kim, New York, NY (US); Natalie J. Gunn, Eltham (AU)

(73) Assignee: International Business Machines Corporation, Armonk, NY (US)

( * ) Notice: Subject to any disclaimer, the term of this patent is extended or adjusted under 35 U.S.C. 154(b) by 35 days.

(21) Appl. No.: 16/111,258

(22) Filed: Aug. 24, 2018

(65) Prior Publication Data

US 2020/0064342 A1    Feb. 27, 2020

(51) Int. Cl.
*B01L 3/00* (2006.01)
*G01N 33/487* (2006.01)
(Continued)

(52) U.S. Cl.
CPC .... *G01N 33/5438* (2013.01); *B01L 3/502715* (2013.01); *G01N 33/566* (2013.01);
(Continued)

(58) Field of Classification Search
CPC ............ G01N 33/5438; G01N 33/566; G01N 27/3278; G01N 33/487; B01L 3/502715;
(Continued)

(56) References Cited

U.S. PATENT DOCUMENTS 7,410,564 B2    8/2008    Flory
8,835,362 B2    9/2014    Downtown et al.
(Continued)

FOREIGN PATENT DOCUMENTS

WO    2004017042 A2    2/2004
WO    2009020682 A2    2/2009

OTHER PUBLICATIONS

Branton et al., "The potential and challenges of nanopore sequencing," NIH Public Access Author Manuscript, May 18, 2009, pp. 1-17, (Published in final form as: Nat Biotechnol. Oct. 2008; 26(10): 1146-1153).
(Continued)

*Primary Examiner* — Tracy Vivlemore
*Assistant Examiner* — Nam P Nguyen
(74) *Attorney, Agent, or Firm* — Kelsey M. Skodje (57) ABSTRACT

A process for monitoring binding events, a coating compound, and a device for monitoring binding events are disclosed. The process includes providing two reservoirs that contain an electrically conductive fluid, wherein the reservoirs are separated by a membrane having a nanopore. The process also includes selecting a target compound, selecting a ligand based on the selection of the target compound, and preparing a coating that includes the coating compound, wherein the coating compound includes the ligand and a moiety that immobilizes the ligand. Additionally, the process includes applying the coating to the inner surface of the nanopore, adding the target compound to a conductive liquid in the first chamber, establishing a voltage gradient across the membrane, and electrically monitoring translocation of the target molecule. The device includes the reservoirs and the membrane having the coated nanopore.

12 Claims, 4 Drawing Sheets

(51) Int. Cl.
*G01N 33/543* (2006.01)
*G01N 33/566* (2006.01)

(52) U.S. Cl.
CPC ... *B01L 2200/12* (2013.01); *B01L 2300/0645* (2013.01); *B01L 2300/123* (2013.01); *B01L 2300/16* (2013.01)

(58) Field of Classification Search
CPC ........... B01L 2200/12; B01L 2300/123; B01L 2300/0645; B01L 2300/16; B01L 2300/161; B01L 2200/0652; B01L 3/00
See application file for complete search history.

(56) References Cited

U.S. PATENT DOCUMENTS

| | | | |
|---|---|---|---|
| 9,453,831 B2* | 9/2016 | Polonsky | G01N 33/54373 |
| 9,791,453 B2 | 10/2017 | Downtown et al. | |
| 10,024,852 B2* | 7/2018 | Gunn | G01N 33/54306 |
| 2010/0025263 A1 | 2/2010 | White et al. | |
| 2010/0331194 A1 | 12/2010 | Turner et al. | |
| 2012/0199483 A1* | 8/2012 | Polonsky | G01N 33/48721 204/519 |
| 2012/0234679 A1 | 9/2012 | Garaj et al. | |
| 2013/0048499 A1 | 2/2013 | Mayer et al. | |
| 2013/0180867 A1 | 7/2013 | Rosenstein et al. | |
| 2014/0152330 A1* | 6/2014 | Afzali-Ardakani | B82Y 30/00 324/693 |
| 2015/0104877 A1* | 4/2015 | Gunn | G01N 33/54306 436/501 |

OTHER PUBLICATIONS

Han et al., "Label-Free Detection of Single Protein Molecules and Protein-Protein Interactions Using Synthetic Nanopores," Analytical Chemistry, vol. 80, No. 12, Jun. 15, 2008, pp. 4651-4658. DOI: 10.1021/ac7025207.

Luan et al., "Tribological Effects on DNA Translocation in a Nanochannel Coated with a Self-Assembled Monolayer," NIH Public Access Author Manuscript, Dec. 30, 2011, pp. 1-12, (Published in final form as: J Phys Chem B. Dec. 30, 2010; 114(51): 17172-17176).

Wanunu et al., "Chemically Modified Solid-State Nanopores," Nano Letters, 2007, vol. 7, No. 6, pp. 1580-1585. 1DOI: 0.1021/nI070462b.

Miles et al., "Single molecule sensing with solid-state nanopores: novel materials, methods, and applications," Chemical Society Reviews, 2013,15-28, DOI: 10.1039/C2CS35286A.

Yusko et al., "Controlling the translocation of proteins through nanopores with bioinspired fluid walls," HSS Public Access Author Manuscript, Oct. 1, 2011, pp. 1-22, (Published in final form as: Nat Nanotechnol. Apr. 2011; 6(4): 253-260).

Wei et al., "Stochastic sensing of proteins with receptor-modified solid-state nanopores," nature nanotechnology, Published Online: Mar. 11, 2012, 33 pages (pp. 1-7, Supplementary Information pp. 1-26). DOI: 10.1038/NNANO.2012.24.

Ding et al., "Capturing Single Molecules of Immunoglobulin and Ricin with an Aptamer-Encoded Glass Nanopore,". NIH Public Access Author Manuscript, Dec. 23, 2010, pp. 1-16, (Published in final form as: Anal Chem. Aug. 15, 2009; 81(16): 6649-6655).

Fox et al., "Autoinduction of Protein Expression," HHS Public Access Author Manuscript, Sep. 18, 2017, pp. 1-25, (Published in final forms as: Curr Protoc Protein Sci. Apr. 2009; Chapter 5: Unite-5.23).

Kim et al., Rapid Fabrication of Uniformly Sized Nanopores and Nanopore Arrays for Parallel DNA Analysis, Advanced Materials, 2006, 18, pp. 3149-3153. DOI: 10.1002/adma.200601191.

Filmore, D., "It's a GPCR World," Modern Drug Discover, Nov. 2004, pp. 24-28.

* cited by examiner

NANOPORE COATING FOR SENSING CHEMICAL BOND FORMATION

BACKGROUND

The present disclosure relates to monitoring translocation of molecules through nanopores and more specifically to surface modification of the nanopore inner surfaces.

Solid state nanopores have applications in single molecule detection. Nanopore-based single molecule sensors can monitor changes in the surface properties of a nanopore caused by translocation of molecules through the pore. For example, changes in ionic current, resistance, or voltage caused by interactions between a molecule and the nanopore inner surface can be monitored. Information that can be determined from these electrical surface measurements can include the size, dimensions, and/or electronic properties of a molecule. Nanopore-based molecule sensors can be used in applications such as biopolymer sequencing, molecule or nanoparticle counting, and molecular size/structure measurements.

SUMMARY

Various embodiments are directed to a process of monitoring binding events. This process can include providing a first reservoir and a second reservoir, wherein the first reservoir and the second reservoir contain an electrically conductive fluid, and wherein the first reservoir and the second reservoir are separated by a membrane that includes a nanopore having an inner surface. The process can also include selecting a target compound, selecting a ligand based on the selection of the target compound, and preparing a coating that includes the selected ligand and a moiety (e.g., hydroxamic acid) for immobilizing the selected ligand on the inner surface. The ligand can be selected from a group of potential ligands identified by computational structure-based screening. Preparing the coating can include modifying the ligand to include the moiety. The process can also include applying the coating to the inner surface of the nanopore, adding the target compound to a conductive liquid in the first chamber, establishing a voltage gradient across the membrane, and electrically monitoring translocation of the target molecule by monitoring changes in ionic current.

Further embodiments are directed to a coating compound that includes a moiety adhering to an inner surface of a nanopore and a ligand linked to the moiety, wherein the ligand is selected based on a selection of a target molecule. In some embodiments, the target molecule is a G protein-coupled receptor protein, and the moiety is a hydroxamic acid moiety. Further, the ligand can be a ligand predicted to bind to a binding site on the target molecule. The ligand can be linked to the moiety by an alkyl chain or a polyethylene glycol unit.

Additional embodiments are directed to a device for monitoring binding events. The device can have reservoirs containing an electrically conductive fluid. The reservoirs are separated by a membrane that includes a nanopore having an inner surface extending through the membrane. The reservoirs and membrane can be integrated into a microfluidic chip. In some embodiments, the membrane is a silicon nitride membrane. The diameter of the nanopore can be in a range of approximately 10 nm-50 nm, and the length of the nanopore can be in a range of approximately 20 μm-75 μm. A coating is disposed on the inner surface of the nanopore. The coating can include moieties bound to the inner surface of the nanopore and ligands selected based on a selection of a target molecule. The device can also include an electronic component, which can include at least one complementary metal-oxide-semiconductor (CMOS) circuit. Further, the device can include silver-silver chloride electrodes.

DETAILED DESCRIPTION

The process of discovery and development for a single new drug can take ten to fifteen years and approximately one billion dollars. The first step in this process, identification and validation of drug candidate compounds, generally takes three to six years, and includes screening thousands of potential compounds. Current screening methods include cell-based techniques wherein a target and a lead compound are identified. The target is a molecule (e.g., RNA, DNA, proteins, etc.) identified as potentially being directly involved in a disease process. The most common categories of targets include proteins such as receptors, enzymes, and ion channels. A lead compound is a chemical compound that has potential therapeutic uses due to its interaction with the target, but requires optimization (e.g., structural modification) before it becomes a true drug candidate.

Transmembrane receptor proteins are proteins that bind or interact with appropriate extracellular species in order to regulate physiological processes within a cell. Herein, extracellular species (e.g., drugs, natural ligands, and lead compounds) that bind to a receptor site are referred to as ligands. Examples of ligands include small molecules, oligomers, and peptides. Ligands generally act as either agonists or antagonists. Agonists cause an action in the cell to happen when they bind to the receptor. Conversely, when antagonists bind to the receptor, they prevent an action from occurring in the cell by blocking agonists.

Examples of receptor proteins include G protein-coupled receptors (GPCRs). There are genes for over 800 different GPCRs in the human genome, and more than 40% of all prescription drugs and drug candidates target these proteins. GPCRs include seven cell membrane-spanning regions, and transduce extracellular stimuli into intracellular signals. Examples of these extracellular stimuli include light, neurotransmitters, odorants, biogenic amines, lipids, proteins, amino acids, hormones, nucleotides, chemokines, and potentially many more. There are approximately three-hundred GPCRs that are of therapeutic interest, and about two-hundred of these have known natural ligands. GPCRs that are of therapeutic interest, but do not have known natural ligands, are commonly known as orphan GPCRs.

Because of the vast number of unique receptor sites and ligands, there are many lead compounds to consider when identifying drug candidates that target GPCRs and other receptor proteins. However, the current cell-based techniques have significant disadvantages. These techniques measure binding of a ligand to a receptor site using fluorescent imaging, which produces data that is difficult to interpret and often contains false positives. Therefore, screenings must be carried out multiple times in order to validate positive results. The efficiency of these methods is also decreased by the necessity of fluorescent labeling, and the large size of fluorescent imaging plates, which limits the number of lead compounds that can be evaluated in a given period of time.

An organic coating and a nanopore-based method of detecting binding events between a target and a ligand are disclosed herein. Nanopore-based detection techniques allow chemical information to be rapidly gathered based on changes in ionic current when single molecules pass through a nanoscale pore (nanopore) in a solid-state membrane. For example, nanopore-based techniques can be used to count molecules or sequence DNA, RNA, and amino acid chains. Herein, the inner surface of a nanopore is coated with a material containing immobilized ligands predicted to bind a target biomolecule. The ligands are linked to moieties that adhere to the surface. Target molecules pass through the nanopore, and chemical interactions (e.g., binding) between the targets and ligands are electronically monitored. This allows the interactions between large number and variety of compounds to be quickly analyzed. For example, an array of nanopore-based detectors can be integrated into a semiconductor chip. Additionally, nanopore sensors offer greater sensitivity than conventional techniques, and the coating acts to decrease signal noise.

Figure 1:
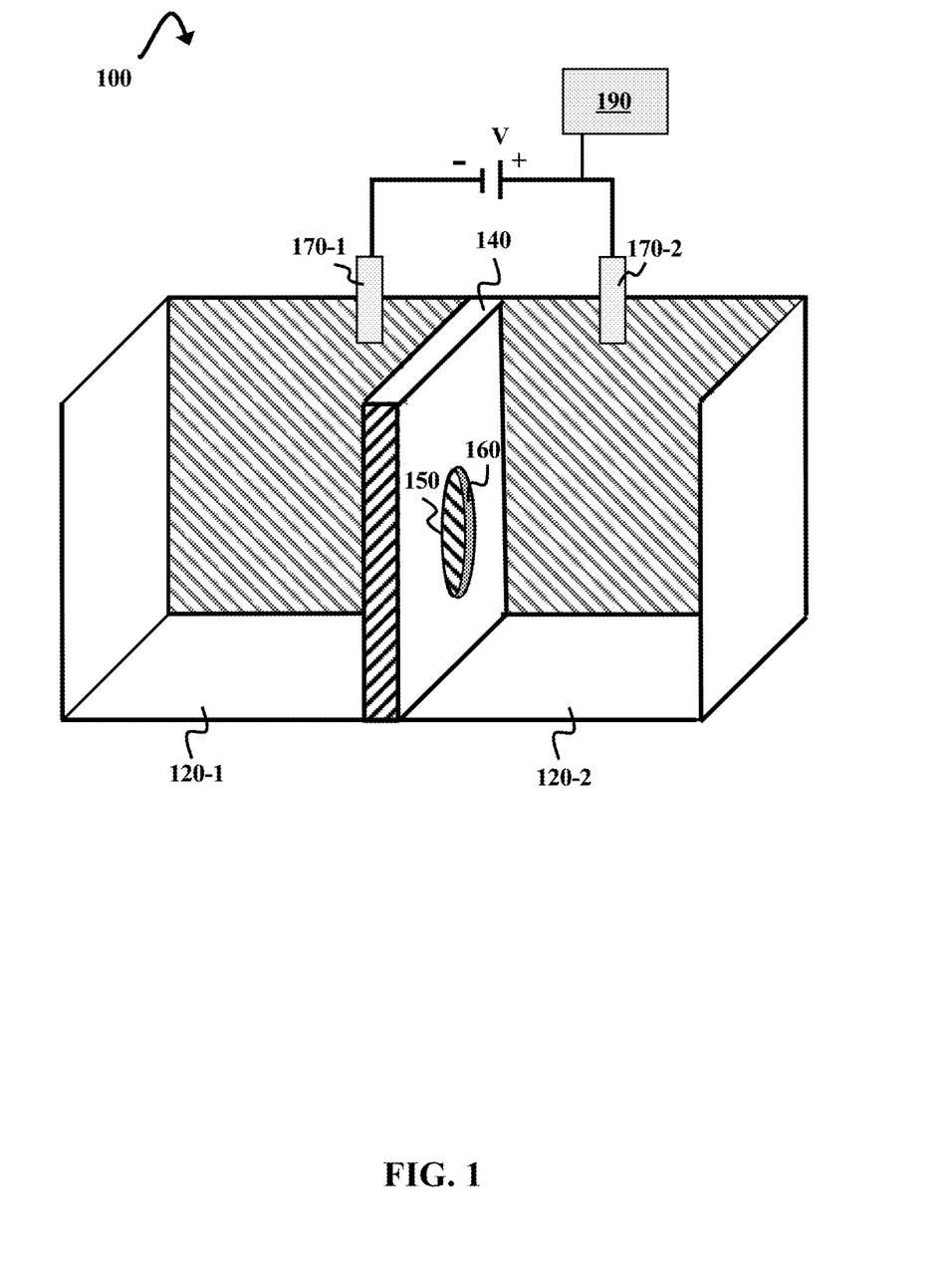
FIG. 1 is a schematic diagram illustrating a nanopore-based sensor environment, according to some embodiments of the present disclosure.

FIG. 1 is a schematic diagram illustrating a nanopore-based sensor environment 100, according to some embodiments of the present disclosure. The sensor 100 includes a first reservoir 120-1 and a second reservoir 120-2 (collectively, 120) separated by a membrane 140. The reservoirs 120 are part of a microfluidic chamber made of a material such as polyether-ether-ketone (PEEK), polydimethylsiloxane, or glass. Examples of inorganic membrane 140 materials that can be used include graphene, glass, silicon, silicon oxide ($SiO_2$), silicon nitride (SiN or $Si_3N_4$), quartz, nitrides, and metals. However, other materials may be used in some embodiments (e.g., polymers). The thickness of the membrane can range from approximately 10 nm to approximately 300 μm.

The membrane 140 includes a nanopore 150 with a diameter of about 10 nm-50 nm. In some embodiments, the nanopore diameter is between about 2 nm-25 nm. However, nanopores of other diameters may be used as well (e.g. approximately 1 nm-500 nm). The nanopore 150 is an aperture in the membrane 140 that allows movement of fluid and particles (e.g., salt ions, molecules, cells, viruses, polymeric particles, organic nanoparticles, etc.) between the reservoirs 120. The nanopore 150 extends through the membrane 140. In some embodiments, the nanopore 150 has a length of about 20 μm-75 μm. The length of the nanopore 150 is the thickness of the membrane 140 when the membrane 140 is uniformly thick. Further, the nanopore includes an inner surface 160 on which an organic coating (not shown) is disposed. Coatings are discussed in greater detail with respect to FIGS. 2 and 3.

The reservoirs 120 contain an electrically conductive fluid (not shown) that is in contact with electrodes 170-1 and 170-2 (collectively, 170). The reservoirs 120 can contain any appropriate electrically conductive fluid. One example of an electrically conductive fluid that can be used is phosphate-buffered saline (PBS). However, solutions of any salts that do not interact destructively with other materials and molecules in solution can be used. Examples of appropriate salts can include potassium chloride (KCl), sodium chloride (NaCl), lithium chloride (LiCl), rubidium chloride (RbCl), and magnesium chloride ($MgCl_2$). In some embodiments, the salt concentration is approximately 1 M-3 M, though other concentrations can be used as well (e.g., 10 mM-5 M). The pH of the electrically conductive fluid can be approximately 5-6, though a pH between about 3 and 11 may also be used. The electrically conductive fluid can be an aqueous solution that optionally contains another solvent, such as ethanol, acetonitrile, and/or dimethylacetamide. Further, the electrically conductive fluid can include a polyacrylamide gel. If a hydrophobic target molecule (e.g., a membrane protein) is selected, detergents or solvent mixtures containing phenol or chloral can be used. A polyacrylamide gel equilibrated in formic acid may also be used for hydrophobic target molecules.

In some embodiments, the electrodes 170 are silver-silver chloride (Ag—AgCl) electrodes. However, the electrodes 170 can also be made from other conductive materials, such as platinum, silver nanowires, copper nanowires, graphene, carbon nanotubes, carbon-sulfur nanotubes, conductive polymers (e.g., poly(3-methylthiphene), poly[3,4-(ethylene-1,2-di-oxy)thiophene], polypyrrole, polyaniline, etc.), and polymer-metal hybrids. Additional examples of materials for the electrodes 170 can include metals such as titanium, indium, yttrium, gadolinium, aluminum, silver, tin, or alloys thereof.

The electrodes 170 are in contact with the conductive solution on either side of the membrane 140. Herein, the side of the membrane 140 facing the first reservoir 120-1 is referred to as the cis side, and the side of the membrane 140 facing the second reservoir 120-2 is referred to as the trans side. The first electrode 170-1 is in contact with electrically conductive fluid in the first reservoir 120-1, and the second electrode 170-2 is in contact with electrically conductive fluid in the second reservoir 120-2. The electrodes 170 are used to establish a voltage gradient across the membrane 140, causing movement of charged particles through the nanopore 150 according to the direction of the gradient and the charge of the particles. This movement through the nanopore 150 is referred to as translocation.

The nanopore-based molecular sensor environment 100 also includes an electronic component 190 for monitoring an ionic current produced during translocation of particles in the electrically conductive fluid. Specifically, the electronic component 190 measures changes in the ionic current flow caused by chemical interactions with the coated inner surface 160. The electronic component 190 can also provide data manipulation, data storage and transfer, amplification, analog-to-digital conversion, signal processing, memory, and/or data output. The electronic component 190 is controlled by a bench-top or portable instrument (not shown). In some embodiments, the electronic component 190 includes at least one complementary metal-oxide-semiconductor (CMOS) circuit.

In some embodiments, the nanopore-based sensor environment 100 is integrated into a microfluidic chip. The microfluidic chip substrate can be a polydimethylsiloxane (PDMS) substrate, though the substrate can also be made of glass, silicon, or any other substrate material. Further, the substrate can be a PDMS/silicon or PDMS/glass substrate. In addition to the reservoirs 120, the microfluidic chip can include microfluidic components such as microchannels, pumps, additional reservoirs, filters, and tubing. In some embodiments, the nanopore molecular sensor environment 100 in a microfluidic chip is part of an array of nanopore-based sensors. For example, one or more chips (e.g., 1-200 chips), each containing at least one nanopore 150, can be integrated into a silicon wafer. The silicon wafer is a semiconducting electronic component 190 that includes circuitry (e.g., CMOS circuits) for controlling the electrodes 170 and microfluidic components. The microfluidic chip can also include an array of nanopores 150.

Figure 2:
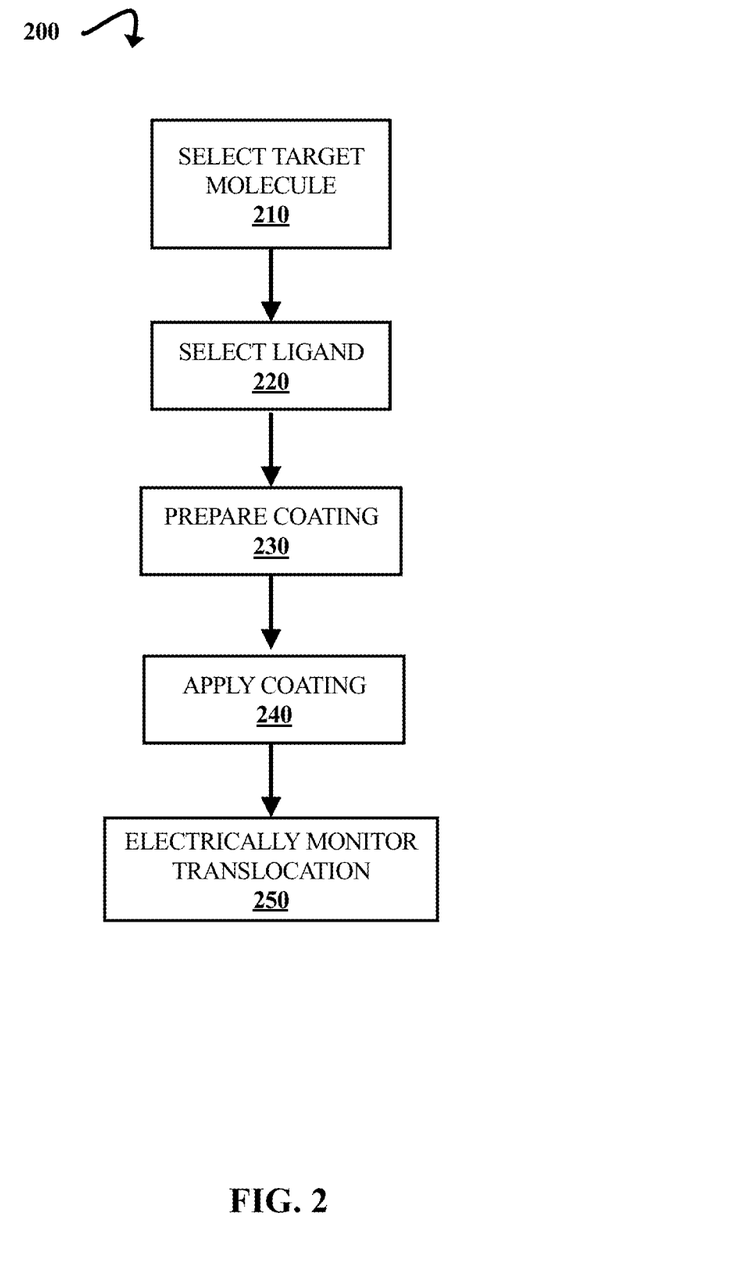
FIG. 2 is a flow diagram illustrating a process of monitoring binding events.

FIG. 2 is a flow diagram illustrating a process 200 of monitoring binding events. To illustrate process 200, but not to limit embodiments, FIG. 2 is described within the context of the nanopore-based sensor environment 100 of FIG. 1. Where elements discussed with respect to FIG. 2 are identical to elements shown in FIG. 1, the same reference numbers are used in both Figures.

Process 200 includes the selection of a target molecule. This is illustrated at step 210. In some embodiments, the target molecule is a G protein-coupled receptor (GPCR). One example of a GPCR that can be selected is neurotensin receptor 1 (NTSR1). Neurotensin receptors are expressed on dopaminergic neurological pathways, and NTSR1 is of interest as a therapeutic target for treating addiction, schizophrenia, Parkinson's disease, colorectal cancer, and other related illnesses. There are a number of compounds known to bind to NTSR1. Agonists for NTSR1 include beta-lactotensin, JMV-449, neurotensin, neuromedin N, PD-149, and the partial agonist TC NTR1 17. Antagonists for NTSR1 include trisubstituted pyrazoles (e.g., SR142948A and SR48692), leucine-derived antagonists, and quinazoline-based antagonists.

Additional examples of GPCRs that can act as target molecules in the nanopore-based sensing environment 100 can include GPCRs that are involved in mediating airway smooth muscle (ASM) functions. Developing drugs that can bind to these mediators is of interest in the treatment of asthma and other causes of airway inflammation. Examples of GPCRs that may be selected based on their ability to mediate ASM functions include m3 muscarinic acetylcholine receptor, Gs-coupled beta-2-andrenergic receptor, E-Prostanoid 2, prostaglandin E2, IP prostacyclin, Gαi-1, Gαi-2, and Gαi-3. However, any GPCR of interest can be selected, such as in urotensin II receptor, angiotensin I and II receptors, histamine receptors, dopamine receptors, serotonin receptors, and acetylcholine receptors.

Targets other than GPCRs can be selected as well, such as enzyme-linked receptor proteins and intracellular receptor proteins. Examples of enzyme-linked receptors that may be selected as target molecules can include receptor tyrosine kinases (e.g., neurotrophin receptors, growth factor receptors, and insulin receptors), receptor guanylate cyclases (e.g., atrial natriuretic peptide (ANP) receptor), receptor tyrosine phosphatases, and receptor serine/threonine kinases (e.g., transforming growth factor-β (TGF-β) receptors). Examples of intracellular receptors that may be selected as target molecules can include steroid hormone receptors (e.g., ecdysone receptors (EcRs), corticosteroid receptors, nuclear estrogen receptors, etc.) and nucleotide-binding oligomerization domain-like receptors (e.g., NOD1, NOD2, inflammasome sensor proteins, etc.).

A ligand is selected based on the target molecule. This is illustrated at step 230. The selected ligand is one that is known or predicted to have a binding interaction with the target molecule. The selected ligands can be analogues of natural ligands or known synthetic ligands for the target molecule, though in some instances the target molecule may have no known natural or synthetic ligands. In some embodiments, ligands are selected with the aid of computational tools. For example, a three-dimensional structure of the target molecule can be determined by computational homology modeling techniques or X-ray crystallography. Using this structural information, potential ligands (e.g., small molecules having structures that may be sterically and electronically appropriate for a binding site on the target molecule) can be located using computational pharmacore and/or structure-based screening.

A coating that includes the selected ligand is prepared. This is illustrated at step 230 The coating immobilizes the selected ligand on the inner surface 160 without inhibiting interactions between the ligand and the target molecule as it passes through the nanopore 150. The ligand is anchored to the inner surface 160 by a moiety capable of adhering to the inner surface 160 of the nanopore 150. For example, a ligand can be linked to a hydroxamic acid moiety by an alkyl chain. However, moieties other than hydroxamic acid for adhering to a nanopore inner surface 160 may be used as well (e.g., silanes, thiols, and phosphonates) in some embodiments. The coating molecules adsorb onto the inner surface 160, forming a self-assembled monolayer with the immobilized ligand facing into the nanopore 150 channel where it can be accessed by the target molecule.

Figure 3:
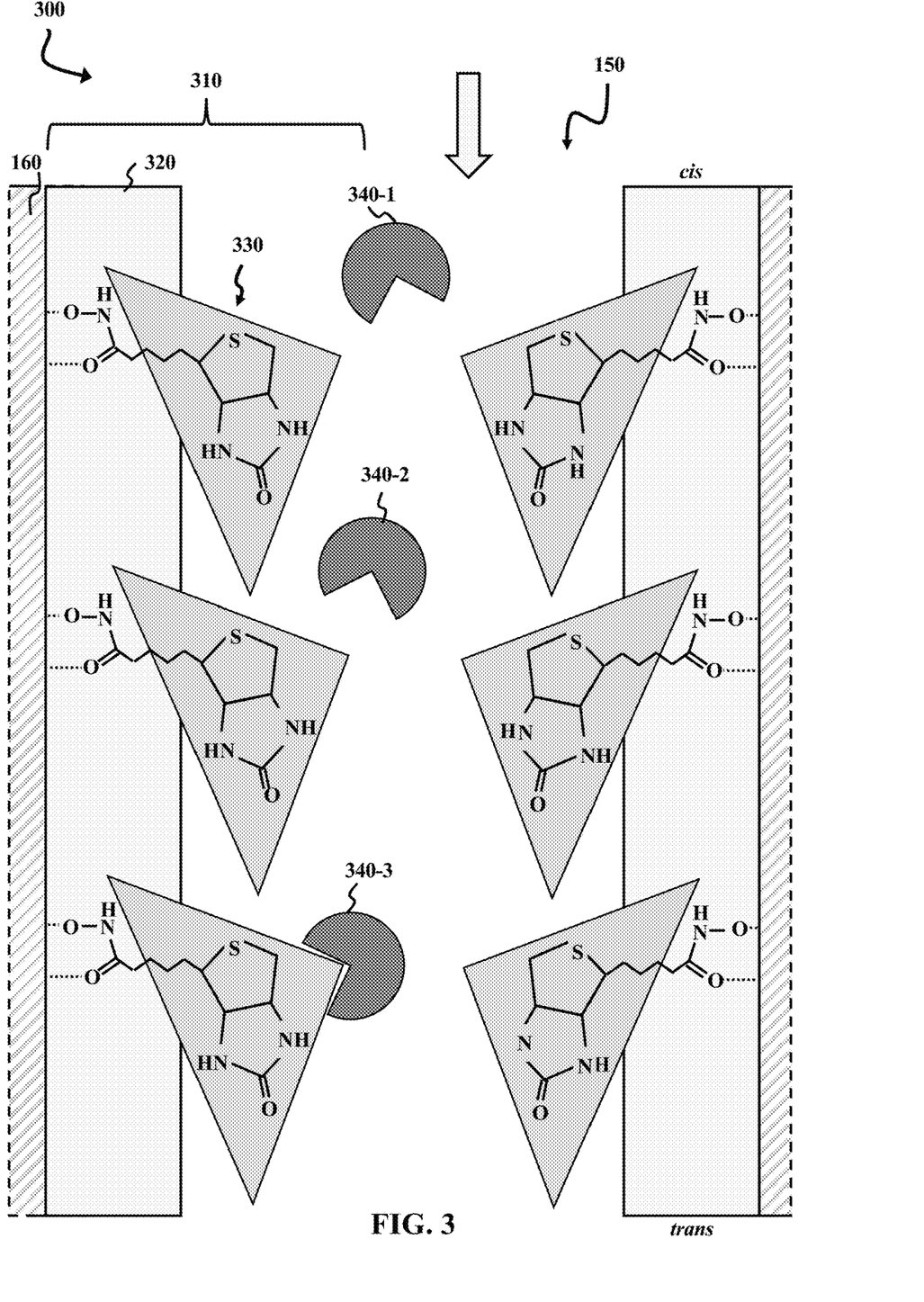
FIG. 3 is a schematic diagram illustrating a cross-sectional view of a coated nanopore environment, according to some embodiments of the present disclosure.

In one illustrative example, a biotin-binding protein, neutravidin, is selected as the target molecule. Neutravidin has a high biotin-binding affinity ($K_a=10^{15}$ $M^{-1}$), and exhibits the lowest nonspecific binding of the known biotin-binding proteins. Therefore, biotin or a biotin analogue can be selected as ligands for neutravidin. Biotin has the structure In order to form a coating with biotin ligands for binding to neutravidin and moieties for immobilizing the ligands, a derivative of biotin having a hydroxamic acid moiety is formed. The original carboxylic acid moiety on biotin is replaced by a hydroxamic acid moiety to form the hydroxamic acid biotin derivative. The structure of this derivative is illustrated in FIG. 3. The hydroxamic acid moiety binds to the inner surface 160 of the nanopore 150. Further, the hydroxamic acid coating reduces signal noise in electronic measurements, allowing current measurements to be determined with high sensitivity. The alkyl chain linking group can also be modified. For example, methylene spacer or polymer groups can be added to lengthen the chain. This is discussed in greater detail below.

The hydroxamic acid moiety can be added to biotin using a variety of methods for synthesizing hydroxamic acids from carboxylic acids. In one example, biotin is combined with ethyl 2-cyano-2-(4-nitrophenylsulfonyloxyimino)acetate, N,N-diisopropylethylamine (DIPEA), and dimethylaminopyridine (DMAP) in tetrahydrofuran (THF). The mixture is allowed to react at room temperature (e.g., 20° C.-30° C.) for approximately thirty minutes. Hydroxylamine hydrochloride is then added to the resulting species in the presence of DIPEA. This mixture is allowed to react for approximately two to three hours, yielding the biotin derivative having the hydroxamic acid moiety. In another example, biotin is combined with hydroxylamine hydrochloride and propylphosphonic anhydride in ethyl acetate (T3P, 50% EtOAc). Approximately two equivalents of n-methylmorpholine (NMM) in acetonitrile are added to the mixture, which is sonicated at room temperature for approximately one hour, resulting in the biotin derivative.

Reactions such as these can also be carried out with compounds other than biotin in order to form hydroxamic acid derivatives with varying ligands. When a selected ligand includes a carboxylic acid moiety that is not necessary for binding to the target molecule, the carboxylic acid moiety can be converted to hydroxamic acid. However, non-hydroxamic acid derivatives may be used in the self-assembling coating in some embodiments. This is discussed in greater detail above. Ligands that do not include appropriate carboxylic acid moieties may be modified to include a carboxylic acid moiety that can be converted to hydroxamic acid. Alternatively, hydroxamic acids having alkyl chains and additional reactive groups (e.g., amines, hydroxyls, carboxylic acids, etc.) can be bound to lead compounds that do not include available carboxylic acid moieties.

The coating is then applied to the inner surface 160 of the nanopore 150. This is illustrated at step 240. The coating can be applied using in situ or ex situ techniques. When the coating is applied ex situ, the membrane 140 is immersed in a solution containing the coating molecules. In an example of this technique, a SiN membrane is dipped in an ethanol/water mixture (e.g., approximately 9:1 EtOH:$H_2O$) containing the biotin derivative, resulting in self-assembly of a biotin derivative coating on the inner surface 160 of the nanopore 150. The membrane 140 is then rinsed in additional solvent to remove excess coating. The thickness, density, and coverage area of the coating can be determined by a variety of characterization techniques. For example, high resolution tunneling electron microscopy (TEM) can be used. Additional examples can include ellipsometry, non-contact atomic force microscopy (AFM), and X-ray photoelectron spectroscopy (XPS).

When the coating is assembled in situ, the coating molecules (e.g., the biotin derivative) are added to an electrically conductive fluid in reservoirs separated by the membrane 140. The reservoirs used for coating can be the reservoirs 120 from the sensor environment 100, though other reservoirs can be used as well. A voltage is applied across the membrane 140, and the coating molecules are driven to the nanopore 150 by the voltage gradient. When the molecules reach the nanopore 150 they adsorb onto the inner surface 160, forming a self-assembled coating layer. The in situ method can help prevent clogging of smaller nanopores (e.g., nanopores having diameters of approximately 5 nm or less). In situ coating can be monitored over time by measuring the decrease in current as the coating is applied.

The interactions between target molecules and ligands can be tuned by modifying the coating. For example, the length of a chemical linker connecting the ligand to the surface-binding moiety can be adjusted by varying the number of methylene spacer groups in the linker. In some embodiments, longer alkyl chains (e.g., 5-20 methylene spacer groups) or polymers (e.g., polyethylene glycol) can be used as spacers between the ligand and the surface-binding moiety. These length adjustments control how deep into the target molecule the ligand can go, which affects the specificity of binding. Additional tuning of the target-ligand interactions can be accomplished by adjusting the applied voltage or the pH, ionic strength, and/or temperature of the electrically conductive fluid.

The binding of the target molecule to the ligand is then monitored by electronic measurements. This is illustrated at step 250. The target molecule (e.g., neutravidin) is added to the electrically conductive fluid so that molecule begins on the cis side of the membrane 140 in the first reservoir 120-1. In some embodiments, the target molecule concentration in the electrically conductive fluid is about 5 µg. However, any target molecule concentration can be used (e.g., approximately 1 µg-10 µg). In one example, neutravidin is added to a 1 M, pH 5 KCl solution in the first reservoir 120-1. However, the electrically conductive fluid composition can vary. Fluid composition options are discussed in greater detail with respect to FIG. 1. When the target molecule is in the electrically conductive fluid, a voltage is applied in order to form a voltage gradient across the membrane 140. In some embodiments, the applied voltage is approximately 175 mV. However, voltages can be selected from a range of approximately 10 mV-500 mV.

The voltage gradient causes charged particles (e.g., the target molecule and salt ions) in the solution to translocate through the nanopore 150. For example, when a 175 mV voltage is applied to a 1 M KCl solution of neutravidin at pH 5 so that the cis side of the membrane 140 is more positively charged than the trans side, positively charged neutravidin molecules and potassium ions ($K^+$) in the first reservoir 120-1 translocate through the nanopore 150 into the second reservoir 120-2. However, the gradient can be reversed in other embodiments. Further, the target molecule can be negatively charged. In the case of proteins, the charge typically depends on the isoelectric point of the protein and the pH of the solution.

In order to enter the second reservoir 120-2, the translocating particles enter the nanopore 150. The salt ions (e.g., $K^+$ and $Cl^-$) are much smaller and lighter than the target molecules, and therefore enter the second reservoir 120-2 before the target molecules. The movement of salt ions produces a baseline current, which is recorded by the electronic component 190. As translocation of the target molecules through the nanopore 150 occurs, the electronic component 190 continues monitoring the ionic current, and detects changes in the current caused by binding events between the target molecule and the coating ligands. In some embodiments, the monitoring time ranges from several seconds to nearly a minute (e.g. 6 s-40 s). However, measurements can be collected for any appropriate length of time (e.g., 10 ms-1 hr.). The length of time it takes for all of the target molecules to reach the nanopore 150 depends on the speed of the target molecule movement within the electrically conductive fluid. This depends on factors such as molecular size and charge.

The electrical component 190 also processes the collected current data, which allows the data to be analyzed. Examples of this processing can include digitizing analogue signals, data leveling, background noise minimization, and generating plotted data (e.g., as current versus time). Current analysis is discussed in greater detail with respect to FIG. 4. Based on the resulting data, a variety of information can be obtained. For example, different target molecules and coating ligands may produce different data signatures when they interact during translocation. These signatures can be used to identify target molecules, ligands, and binding events. Additionally, the current monitoring can be used in conjunction with optical detection methods, such as fluorescence spectroscopy and/or total internal reflection fluorescence (TIRF) spectroscopy.

FIG. 3 is a schematic diagram illustrating a cross-sectional view of a coated nanopore environment 300, according to some embodiments of the present disclosure. To illustrate this environment 300, but not to limit embodiments, FIG. 3 is described within the context of the nanopore-based sensor environment 100 of FIG. 1. Where elements shown in FIG. 3 are identical to elements shown in FIG. 1, the same reference numbers are used in both Figures.

The inner surface 160 of the nanopore 150 is coated with a self-assembled biotin derivative coating 310. For simplicity, only side walls of the nanopore 150 are illustrated in FIG. 3. Further, only one of the two illustrated inner surface 160 walls includes reference numbers. However, the reference numbers refer to identical elements on each side. The inner surface 160 is illustrated as having an exterior dashed line. This indicates that the inner surface 160 is part of a membrane 140 separating reservoirs 120 in the nanopore-based molecular sensor 100. In some embodiments, the membrane 140 is a silicon nitride (SiN) membrane. However, other materials can be used. This is discussed in greater detail with respect to FIG. 1. The inner surface 160 is the same material as the membrane 140.

The coating 310 is a biotin derivative layer having a hydroxamic acid component 320 (surrounded by a light gray box) and biotin ligand components 330 (surrounded by darker gray triangles). The hydroxamic acid component 320 includes hydroxamic acid moieties that immobilize the biotin ligands 330 on the inner surface 160. Only three biotin derivative molecules in the coating 310 are illustrated on each side. However, this is to simplify the illustration, and the inner surface 160 is coated more thoroughly. The number of ligands from biotin derivatives 340 adhering to the inner surface 160 depends upon the surface area and the density and thickness of the coating. The density and thickness of the coating depend on factors such as the coating technique (e.g., length of time the membrane is immersed in the coating solution and/or concentration of ligand coating molecules in the coating solution) and the structure of the coating compounds. In some embodiments, the coating has a thickness of approximately 1.2 nm. However, other thicknesses are possible (e.g., approximately 1 nm-5 nm).

The illustrated biotin ligands 330 are surrounded by gray triangles in order to indicate that their structure allows them to selectively bind to neutravidin target molecules 340-1, 340-2, and 340-3 (collectively 340). The neutravidin target molecules 340 are illustrated as dark gray circles having triangular cut-outs representing biotin binding sites. It will be understood by a person of ordinary skill in the art that the shape and relative size of the target molecules 340 are for illustrative purposes only, and do not accurately represent these features of neutravidin. For example, a molecule of neutravidin has a mass of approximately 60,000 daltons, and includes four biotin binding sites. Further, the dimensions of a neutravidin molecule are approximately 5.6 nm×5 nm×4 nm.

A gray block arrow indicates the direction of translocation of the target molecules 340 through the nanopore 150. The target molecules 340 translocate from the cis to the trans side of the membrane 140 when a voltage gradient is applied. One of the target molecules 340-3 is illustrated as being bound to a biotin ligand 330, while the others 340-1 and 340-2 are still in the process of translocating. The binding of this molecule 340-3 causes a change in the ionic current. The other target molecules 340-1 and 340-2 may bind to additional biotin ligands. For simplicity, only three target molecules 340 are illustrated. However, the number of molecules 340 translocating through the nanopore 150 depends upon factors such as the target molecule 340 concentration in the electrically conductive fluid, the size of the nanopore 150, and the thickness of the coating 310.

Figure 4:
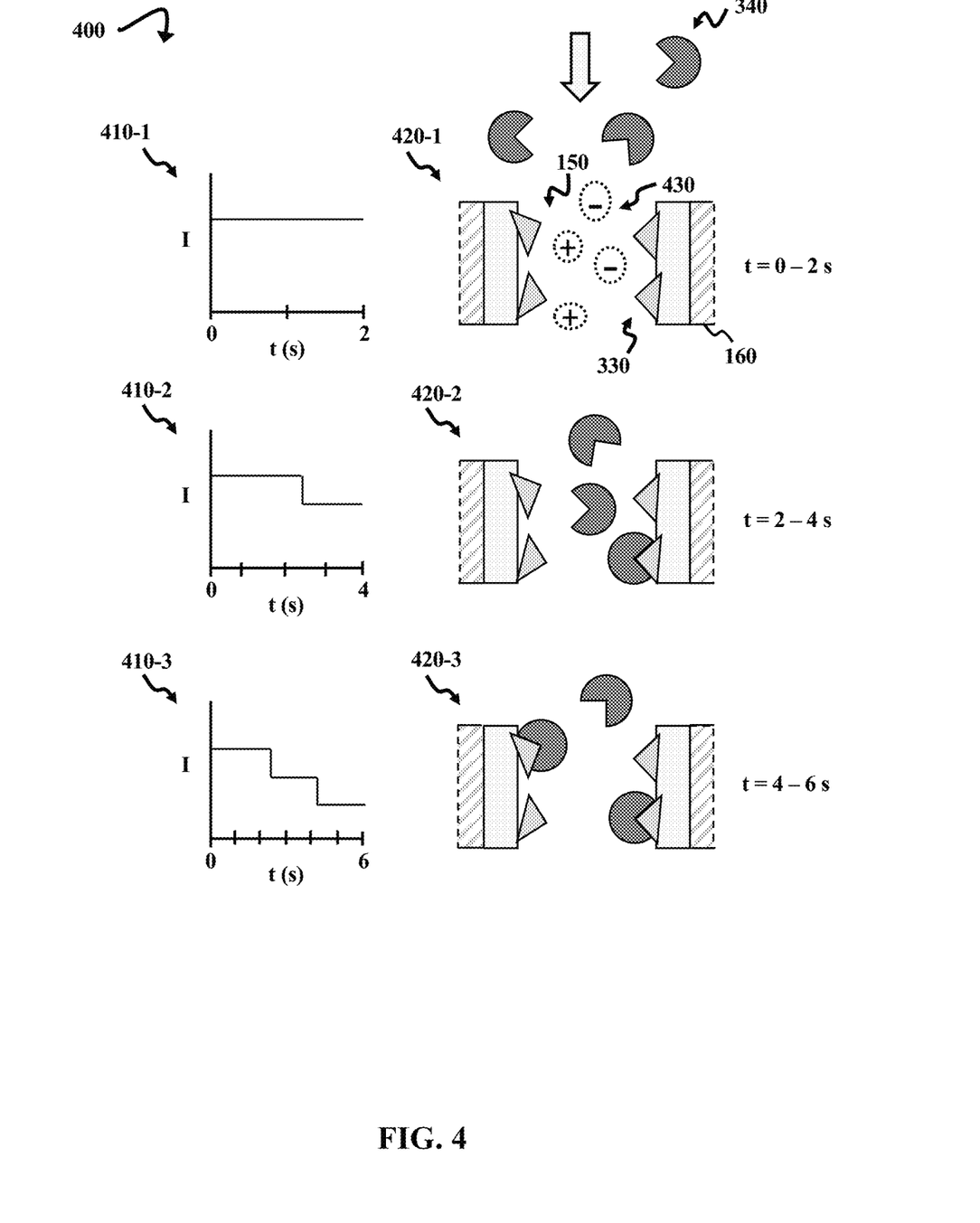
FIG. 4 is a schematic diagram illustrating example data collection during current monitoring, according to some embodiments of the present disclosure.

FIG. 4 is a schematic diagram illustrating example data collection 400 during current monitoring, according to some embodiments of the present disclosure. To illustrate this example, but not to limit embodiments, FIG. 4 is described within the context of the nanopore environments 100 and 300 of FIGS. 1 and 3. Where elements shown in FIG. 4 are identical to elements shown in FIGS. 1 and 3, the same reference numbers are used in each Figure. Further, the processes discussed with respect to FIG. 4 substantially correspond to the current monitoring processes carried out at step 250 of process 200. This is described in greater detail with respect to FIG. 2.

Changes in ionic current caused by binding of the neutravidin target molecules 340 to the biotin ligands 330 are monitored. The collected current data is processed by the electrical component 190. From ionic current data collected over a period of six seconds, three plots 410-1, 410-2, and 410-3 (collectively 410) of current (I) versus time (t) are generated. Translocation through the nanopore 150 is diagrammatically illustrated at stages 420-1, 420-2, and 420-3 (collectively 420) corresponding to portions of the six-second monitoring period. The direction of charged particle movement caused by an applied voltage gradient is represented by a gray block arrow. Elements in the next stages 420-2 and 420-3 in this process 400 are illustrated without reference numbers in order to simplify the figure. However, these elements are illustrated in the same way in each diagram, and therefore are indicated by the reference numbers of the first stage 420-1.

The first plot 410-1 shows a baseline ionic current produced during the translocation stage 420-1 taking place during the first two seconds of monitoring. The baseline ionic current is produced by translocation of the high-mobility salt ions 430 (e.g., $K^+$ and $Cl^-$, $Na^+$ and $Cl^-$, or $Mg^{2+}$ and 2 $Cl^-$) through the nanopore 150. The ions 430 are illustrated as ovals with dashed lines surrounding charge symbols. Because of the small size and low mass of the ions 430, they move quickly through the nanopore 150. Further, the ions 430 are small enough that they do not interact substantially with the coating 310 or the inner surface 160. Therefore, no substantial current changes are detected in the first two seconds.

In the second stage 420-2, which takes place over the third and fourth seconds of translocation monitoring, the neutravidin target molecules 340 begin to enter the nanopore 150. A target molecule 340 selectively binds to a biotin ligand 330. This binding causes a change in the ionic current, which can be observed as a drop in current in the second plot 410-2. The second plot 410-2 includes current data for the first four seconds of the process 400. In the third stage 420-3, a second target molecule 340 binds to a second biotin ligand in the coating 310. This stage 420-3 takes place over the fifth and sixth seconds in the monitoring process 400. Again, this binding causes a current change. The third plot 410-3 displays data collected for the first six seconds of the process, which includes both drops in current caused by binding events. Therefore, the plots 410 of current versus time indicate that two target molecules 340 formed bonds with two ligands 330 during the six seconds of monitoring.

The processes discussed herein and their accompanying drawings are not to be construed as limiting. One skilled in the art would recognize that a variety of nanopore-based detection system configurations may be used that vary in conditions, components, methods, etc., which include a nanopore having an inner surface coated with ligands selected based on target molecules. In addition, the conditions can optionally be changed over the course of a process. Further, in some embodiments, processes can be added or omitted while still remaining within the scope of the disclosure, as will be understood by a person of ordinary skill in the art.

What is claimed is:

1. A process of monitoring binding events, comprising:
   providing a first reservoir and a second reservoir, wherein the first reservoir and the second reservoir contain an electrically conductive fluid, and wherein the first reservoir and the second reservoir are separated by a membrane that includes a nanopore having an inner surface;
   selecting a target compound;
   preparing a biotin derivative having hydroxamic acid moiety;
   preparing a solution of the biotin derivative;
   adding the solution to the first reservoir;
   establishing a voltage gradient across the membrane;
   electrically monitoring formation of a coating on the inner surface of the nanopore, wherein the coating comprises molecules of the biotin derivative immobilized by adherence of the hydroxamic acid moiety to the inner surface;
   rinsing the membrane with a solvent to remove excess molecules of the biotin derivative;
   adding a solution of the target compound in a conductive liquid to the first chamber;
   establishing a voltage gradient across the membrane; and
   electrically monitoring translocation of the target molecule.

2. The process of claim 1, wherein the biotin derivative is selected from a group of potential ligands identified by computational structure-based screening.

3. The process of claim 1, wherein the electrically monitoring translocation comprises monitoring changes in ionic current in the electrically conductive fluid.

4. A device for monitoring binding events, comprising:
   two reservoirs containing an electrically conductive fluid;
   a membrane separating the two reservoirs, wherein the membrane includes a nanopore having an inner surface extending through the membrane; and
   a coating disposed on the inner surface of the nanopore, wherein the coating includes a self-assembled layer of biotin derivative molecules having hydroxamic acid moieties bound to the inner surface of the nanopore, and wherein the biotin derivative molecules are selected based on a selection of a target molecule.

5. The device of claim 4, further comprising an electronic component.

6. The device of claim 5, wherein the electronic component includes at least one complementary metal-oxide-semiconductor circuit.

7. The device of claim 4, further comprising two electrodes.

8. The device of claim 7, wherein the two electrodes are silver-silver chloride electrodes.

9. The device of claim 4, wherein the diameter of the nanopore is in a range of approximately 10 nm 50 nm.

10. The device of claim 4, wherein the length of the nanopore is in a range of approximately 20 μm-75 μm.

11. The device of claim 4, wherein the two reservoirs and the membrane are integrated into a microfluidic chip.

12. The device of claim 4, wherein the membrane is a silicon nitride membrane.

* * * * *